United States Patent
El Jamali et al.

(10) Patent No.: US 10,564,168 B2
(45) Date of Patent: Feb. 18, 2020

(54) METHOD FOR TREATING MALE INFERTILITY BASED ON NOX5 PROTEIN LEVELS IN SPERM

(71) Applicants: Amina El Jamali, San Antonio, TX (US); Veronique Barnes, San Antonio, TX (US)

(72) Inventors: Amina El Jamali, San Antonio, TX (US); Veronique Barnes, San Antonio, TX (US)

(*) Notice: Subject to any disclaimer, the term of this patent is extended or adjusted under 35 U.S.C. 154(b) by 0 days.

(21) Appl. No.: 15/584,476

(22) Filed: May 2, 2017

(65) Prior Publication Data

US 2018/0074071 A1 Mar. 15, 2018

Related U.S. Application Data

(63) Continuation of application No. 15/331,971, filed on Oct. 24, 2016, now abandoned, which is a continuation of application No. 14/167,396, filed on Jan. 29, 2014, now abandoned.

(60) Provisional application No. 61/758,178, filed on Jan. 29, 2013.

(51) Int. Cl.
*G01N 33/68* (2006.01)

(52) U.S. Cl.
CPC ................................ *G01N 33/689* (2013.01)

(58) Field of Classification Search
None
See application file for complete search history.

(56) References Cited

U.S. PATENT DOCUMENTS

| | | | |
|---|---|---|---|
| 2013/0143879 A1 | 6/2013 | Page | 514/234.2 |
| 2013/0158027 A1 | 6/2013 | Page | 514/234.2 |
| 2013/0296362 A1 | 11/2013 | Page | 514/303 |

OTHER PUBLICATIONS

Ghani et al., Andrologia, 2013; 45: 351-356 (Year: 2013).*
Cifuentes-Pagano et al., Curr Pharm Des. Author manuscript; available in PMC Apr. 2, 2016; 28 pages total (Year: 2016).*
Mussett et al., JBC, 2012; 287: 9376-9388 (Year: 2012).*
Aitken et al., Free Radic. Biol. Med., 2004, 36, 994-1010.
Aitken et al., Handb Exp. Pharmacol., 2010, 198, 99-11547.
Aitken et al., J. Androl., 2000,21,491-496.
Aitken et al., J. Reprod. Fertil. Suppl., 1998,53, 109-118.
Aitken et al., Int. J. Androl., 1990, 13, 433-451.
Aitken et al., Reprod. Fertil. Dev., 1994, 6, 19-23.
Aitken etal., J. Gell. Sei., 1998,111,645-656.
Armstrong et al., Int. J. Androl., 2002, 25, 223-229.
Banfi et al., J. Biol. Chem., 2001, 276, 37594-37601.
Banfi et al., J. Biol. Chem., 2004, 279, 18583-18591.
Belaiba et al., Free Radie. Biol. Med., 2007, 42, 446-459.
Brar et al., Am. J. Physiol. Gell. Physiol., 2003, 285, G353-369.
Cheng et al., Gene, 2001,269, 131-140.
Cucoranu et al., Circ. Res., 2005, 97, 900-907.
De Lamirande et al., Free Radic. Bio I. Med., 2009, 46, 502-51 0.
De Lamirande et al., Free Radic. Biol. Med., 1993, 14, 157-166.
De Lamirande et al., J. Androl. 1998, 19, 585-594.
De Lamirande et al., J. Androl., 1992, 13, 368-378.
De Lamirande etal., Biochim. Biophys. Acta., 2008,1784, 106-115.
Decoursey et al., Physiology (Bethesda, Md.), 2010, 25, 27-40.
El Ghemaly et al., J. Exp. Med., 2010,207. 129-S121-122.
El Jamali et al.. Free Radic. Biol. Med .. 2008. 44. 868-881.
Florman et al., Gell, 2010, 140, 310-312.
Ford et al., Int. J. Androl. 1997, 20, 44-49.
Fulton et al., Antioxid. Redox. Signal. 2009, 11, 2443-2452.
Garcia et al., Mol. Reprod. Dev., 1999, 52, 189-195.
Hong et al., Cancer Res., 2010,70, 1247-1255.
Jagnandan et al., J. Biol. Ghem., 2007, 282, 6494-6507.
Jay et al., Free Radie. Biol. Med., 2008,45, 329-335.
Kamiguti et al., J. lmmunol., 2005, 175, 8424-8430.
Kessopoulou et al., J. Reprod. Fertil. 1992, 94, 463-470.
Laleu et al., J. Med. Ghem., 2010, 53,7715-7730.
Lishko et al., Cell, 2010, 140, 3273-3729.
Lishko et al., Nature, 2011, 471, 387-391.
Morgan et al., J. Physiol., 2007, 579, 327-344.
Morgan et al., Proe. Natl. Acad. Sei. USA, 2009, 106, 18022-18027.
Moustafa et al., Hum. Reprod., 2004, 19, 129-138.
Musset et al., J. Physiol., 2008, 586, 2477-2486.
Mussett et al., The J. Biol. Chem., 2012,287 (12) 9376-9388.
Neri-Vidaurri et al., Biochem. Biophys. Res. Commun., 2006, 343, 105-109.
Petheo et al., PloS. One. 2010, 5, e14081.
Ramsey et al., Proe. Natl. Aead. Sei. Usa, 2009 106, 7642-7647.
Richer et al., Mol. Hum. Reprod., 2001, 7, 237-244.
Rivlin et al., Biol. Reprod., 2004,70, 518-522.
Sabeur et al., Reproduction, 2007, 134, 263-270.
Salles et al., Exp. Geraniol., 2005, 40, 353-357.
Sedeek et al., Am. J. Physiol. Renal. Physiol., 2010, 299, F1348-F1358.
Serrander et al., Biochimie, 2007; 89: 1159-1167.
Whittington et al., Int. J. Androl., 1999, 22, 229-235.
Zeng et al., Dev. Biol., 1996, 173, 510-520.

* cited by examiner

*Primary Examiner* — Christina M Borgeest
(74) *Attorney, Agent, or Firm* — Norton Rose Fulbright US LLP

(57) ABSTRACT

Certain embodiments include methods of assessing male fertility.

3 Claims, 7 Drawing Sheets

METHOD FOR TREATING MALE INFERTILITY BASED ON NOX5 PROTEIN LEVELS IN SPERM

PRIORITY CLAIM

This application is a continuation from U.S. Ser. No. 15/331,971 filed Oct. 24, 2016, which is a continuation from U.S. Ser. No. 14/167,396 filed Jan. 29, 2014 which claims priority to U.S. 61/758,178 filed Jan. 29, 2013, which are each incorporated herein by reference in their entirety.

STATEMENT REGARDING FEDERALLY FUNDED RESEARCH

This invention was made with government support under RR025767, DK084297, and HL007446 awarded by the National Institutes of Health. The government has certain rights in the invention.

BACKGROUND

MacLeod demonstrated as early as 1943 that spermatozoa were able to generate ROS (MacLeod (1943) *Am. J. Physiol.* 138, 512-518). ROS production by spermatozoa correlates with lipid peroxidation, DNA oxidation, poor sperm function, and reduced fertility (Aitken (1994) *Reprod. Fertil. Dev.* 6, 19-23, discussion 23-24; Moustafa et al. (2004) *Hum. Reprod.* 19, 129-138). However, recent evidence suggests that redox activity is physiologically important in promoting normal sperm function (De Lamirande and Gagnon (1992) *J. Androl.* 13, 368-378; Aitken (2000) *J. Androl.* 21, 491-496; De Lamirande and Lamothe (2009) *Free Radic. Biol. Med.* 46, 502-510). Generation of ROS is required for sperm capacitation, the final maturation steps associated with hyperactive motility and a physiological acrosome reaction (De Lamirande and Gagnon (1993) *Free Radic. Biol. Med.* 14, 157-166; Aitken et al. (2004) *Free Radic. Biol. Med.* 36, 994-1010). In spite of evidence for both physiologic and pathologic effects of ROS in spermatozoa, the identity of the ROS-producing enzyme(s) remains uncertain.

SUMMARY

Certain embodiments are directed to measuring or detecting NOX5 protein levels in human spermatozoa. Moreover, the regulation of NOX5 by H2O2 is mediated by Ca2+ entry and c-Abl tyrosine kinase activation, while the downstream ROS generation is implicated in spermatozoa motility. Taken altogether, our results suggest that the expression levels and/or activities of NOX5, c-Abl, and HV1 are significant determinants of the redox status of human spermatozoa and consequently their motility and ovum-fertilizing potential. Moreover, NOX5 and the proteins regulating its activity represent new therapeutic targets for either male infertility (if NOX5 is hyperactive) or male contraception (if NOX5 is physiologically active).

Certain aspects are directed to methods of assessing male fertility comprising extracting proteins from a sperm or semen sample obtained from a subject and measuring the level of NOX5 protein in the sperm or semen sample, wherein a level of NOX5 protein is at least 10 fold lower or at least 10 fold higher relative to a normal reference level is indicative of male infertility. The methods can further comprising measuring protein levels for cAb1 and HV1 proteins, wherein a decrease in protein levels is indicative of infertility. In certain aspects the level of NOX5 protein is at least 5, 10, 15, 20, 40, 50, 60, 80, 90, or 100 fold lower or at least 5, 10, 15, 20, 40, 50, 60, 80, 90, or 100 fold higher than a reference level.

In a further aspect the methods are directed to in vitro diagnosis of male infertility comprising measuring the level of NOX5 protein in a sperm sample from a subject using at least one antibody that specifically binds NOX5; and diagnosing the subject with infertility when the level of NOX5 protein is decreased relative to a reference, the decreased level being indicative of infertility. In certain aspects the level of NOX5 protein is at least 5, 10, 15, 20, 40, 50, 60, 80, 90, or 100 fold lower or at least 5, 10, 15, 20, 40, 50, 60, 80, 90, or 100 fold higher than a reference level. The methods can further comprise measuring protein levels for cAb1 and HV1 proteins, wherein a decrease in protein levels is indicative of infertility.

In certain aspects the methods are directed to assessing sperm function comprising extracting proteins from a sperm or semen sample obtained from a subject and measuring the level of NOX5 protein in the sperm or semen sample, wherein a decrease in the level of NOX5 protein relative to a normal reference level is indicative of reduced sperm motility. In certain aspects the level of NOX5 protein is at least 5, 10, 15, 20, 40, 50, 60, 80, 90, or 100 fold lower or at least 5, 10, 15, 20, 40, 50, 60, 80, 90, or 100 fold higher than a reference level. The methods can further comprise measuring protein levels for cAb1 and HV1 proteins, wherein a decrease in protein levels is indicative of infertility.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 5A-5D. Superoxide production by NOX5 requires HV1. (A) Superoxide production by K562/NOX5 cells pre-incubated for 5 min with or without 1 mM ZnCl2 and then stimulated with either ionomycin (1 µM), PMA (1 µg/ml) or H2O2 (100 µM) was measured and expressed as in FIG. 2. The data expressed are the means+/−SEM of 6 independent experiments. Hash signs indicate statistical significance versus stimulated cells in the absence of ZnCl2. ###P<0.001. (B) K562/NOX5 cells were transiently transfected with scrambled siRNA or HV1-specific siRNA and tested for superoxide production stimulated by H2O2 (100

µM), ionomycin (1 µM), or PMA (1 µg/ml). Immunoblot analysis using HV1 antibody (above) was performed to ensure that the down-regulation of HV1 protein by siRNA was effective. Actin antibody was used to control for protein loading. The data expressed are the means+/−SEM of 5 independent experiments. The hash signs indicate statistical significance versus stimulated cells transfected with scrambled siRNA. ##P<0.01; ###P<0.001. (C) Immunoprecipitation of NOX5 or HV1 protein was performed using total protein lysates isolated from K562 cells or K562/NOX5 cells. The content of the immunoprecipitates was analyzed by immunoblot using HV1 and NOX5 antibodies. The results are representative of 3-5 experiments. (D) Families of proton currents were recorded during pulses in 10 mV increments up to +60 mV in K562 cells (lower tracings) and K562/NOX5 cells (upper tracings) before and then after stimulation with PMA (60 nM), and finally after addition of GFX (3 µM).

DESCRIPTION

Physiological and pathological processes in spermatozoa involve the production of reactive oxygen species (ROS), but the identity of the ROS-producing enzyme system(s) remains a matter of speculation. The inventors provide evidence that NOX5 NADPH oxidase is expressed and functions in human spermatozoa. Immunofluorescence microscopy detected NOX5 protein in both the flagella/neck region and the acrosome. Functionally, spermatozoa exposed to calcium ionophore, phorbol ester, or $H_2O_2$ exhibited superoxide anion production, which was blocked by addition of superoxide dismutase, a Ca2+ chelator, or inhibitors of either flavoprotein oxidases (diphenylene iodododonium) or NOX enzymes (GKT136901). Consistent with previous over-expression studies, the inventors found that $H_2O_2$-induced superoxide production by primary sperm cells was mediated by the non-receptor tyrosine kinase c-Abl. Moreover, the HV1 proton channel, which was recently implicated in spermatozoa motility, was required for optimal superoxide production by spermatozoa. Immunoprecipitation experiments suggested an interaction among NOX5, c-Abl, and HV1. $H_2O_2$ treatment increased the proportion of motile sperm in a NOX5-dependent manner. Statistical analyses showed a pH-dependent correlation between superoxide production and enhanced sperm motility. Collectively, the findings show that NOX5 is a major source of ROS in human spermatozoa and indicate a role for NOX5-dependent ROS generation in human spermatozoa motility

I. NADPH OXIDASE, EF-HAND CALCIUM BINDING DOMAIN 5 (NOX5)

Numerous studies have shown a similarity between the ROS-producing enzyme in spermatozoa and the enzymatic system expressed in phagocytes. In phagocytes, the major ROS precursor is the superoxide anion generated by the single-electron reduction of molecular oxygen by the NOX2 NADPH oxidase complex. NOX5 is a novel isoform of the NOX family of NADPH oxidases that is activated by the binding of Ca2+ to its cytosolic N-terminal EF-hand domains (Banfi et al. (2001) *J. Biol. Chem.* 276, 37594-37601; Banfi et al. (2004) *J. Biol. Chem.* 279, 18583-18591). It is suggested that Ca2+ binding induces a conformational change leading to the interaction of the N-terminus of NOX5 with its C-terminal substrate-binding and flavin-containing domains, thereby inducing ROS production (Banfi et al. (2001) *J. Biol. Chem.* 276, 37594-37601; Banfi et al. (2004) *J. Biol. Chem.* 279, 18583-18591). Among the five splice variants identified, NOX5α, NOX5β, NOX5γ, and NOX5δ (all long forms of NOX5 designated collectively as NOX5L) differ in the N-terminal sequences of their Ca2+-binding domains, whereas the truncated NOX5S (short) variant lacks the Ca2+-binding domains altogether (Fulton (2009) *Antioxid. Redox. Signal.* 11, 2443-2452). Although the NOX5 gene is widely conserved evolutionarily, it is curiously absent from rodent genomes (Cheng et al. (2001) *Gene* 269, 131-140). NOX5 has been found in a prostate carcinoma cell line (Brar et al. (2003) *Am. J. Physiol. Cell. Physiol.* 285, C353-369), hairy cell leukemia B-cells (Kamiguti et al. (2005) *J. Immunol.* 175, 8424-8430), endothelial cells (BelAiba et al. (2007) *Free Radic. Biol. Med.* 42, 446-459), smooth muscle cells (Jay et al. (2008) *Free Radic. Biol. Med.* 45, 329-335), stomach (Salles et al. (2005) *Exp. Gerontol.* 40, 353-357), cardiac fibroblasts (Cucoranu et al. (2005) *Circ. Res.* 97, 900-907), and Barrett's esophagus epithelia (Hong et al. (2010) *Cancer Res.* 70, 1247-1255).

NOX5 mRNA was initially detected in human testis in 2001 (Banfi et al. (2001) *J. Biol. Chem.* 276, 37594-37601), and a Ca2+ ionophore was shown to induce ROS generation in human spermatozoa (De Lamirande et al. (1998) *J. Androl.* 19, 585-594). In 2007 NOX5 protein was detected by immunoblot analysis in equine sperm (Sabeur and Ball (2007) *Reproduction* 134, 263-270). Although these observations suggest that spermatozoa might express NOX5, it was not certain that NOX5 was expressed at the protein level in human spermatozoa. The inventors have documented both the expression and function of NOX5 in human spermatozoa.

Both physiologic and pathologic effects of ROS in spermatozoa have been described, but the identity of the ROS-producing enzyme(s) has remained unknown. Here, the inventors describe NOX5 expression and function in human spermatozoa and that NOX5 activity is needed for spermatozoa motility.

Spermatozoa released from the testis are transcriptionally inert (Sotolongo and Ward (2000) *J. Cell. Biochem. Suppl.* 35, 23-26) and yet they undergo functional maturation to acquire ovum-fertilizing ability. These changes are believed to occur through the modulation of biochemical pathways and cellular properties by incoming signals from the sperm microenvironment, including ROS (Aitken et al. (2010) *Handb. Exp. Pharmacol.* 198, 99-11547). The putative ROS-producing enzyme has been compared with the NADPH oxidase expressed in phagocytic leukocytes (Armstrong et al. (2002) *Int. J. Androl.* 25, 223-229). Some studies have even suggested that spermatozoa themselves do not possess NADPH oxidase activity (Armstrong et al. (2002) *Int. J. Androl.* 25, 223-229; Ford et al. (1997) *Int. J. Androl.* 20, 44-49; Richer and Ford (2001) *Mol. Hum. Reprod.* 7, 237-244), but rather that ROS generation is attributable to leukocytes that may be present in some sperm preparations (Aitken and West (1990) *Int. J. Androl.* 13, 433-451; Kessopoulou et al. (1992) *J. Reprod. Fertil.* 94, 463-470; Whittington and Ford (1999) *Int. J. Androl.* 22, 229-235). The data described herein show that spermatozoa express their own ROS-producing enzyme, namely one or more of the long splice variants of NOX5 NADPH oxidase, which produce superoxide in a Ca2+-dependent manner. Since a qPCR approach is precluded by the fact that spermatozoa are transcriptionally inert, human sperm samples were tested for other NOX isoforms by immunoblot analyses using antibodies specific for NOX1, 2, and 4; no signal for these NOX proteins was detected. NOX5 is the predominant NOX family NADPH oxidase in human spermatozoa.

It was reported previously (El Jamali et al. (2008) *Free Radic. Biol. Med.* 44, 868-881) that $H_2O_2$ positively regulates NOX5β via a Ca2+/c-Abl-dependent pathway. The results described herein demonstrate that this regulation is also operative in human spermatozoa, both the Ca2+ chelator BAPTA and the c-Abl tyrosine kinase inhibitor imatinib mesylate abrogated $H_2O_2$-induced superoxide production. Furthermore, evidence is provided that a functional complex between NOX5 and c-Abl exist in human spermatozoa. ROS-induced tyrosine phosphorylation of several unidentified proteins appears to be essential for sperm capacitation (Aitken et al. (1998) *J. Cell. Sci.* 111, 645-656). Two major spermatozoal proteins with molecular sizes similar to NOX5L and c-Abl have been reported to be regulated by PKA and by $H_2O_2$ in a protein tyrosine phosphatase-independent manner (De Lamirande and Lamothe (2009) *Free Radic. Biol. Med.* 46, 502-510; Aitken et al. (1998) *J. Cell. Sci.* 111, 645-656; Rivlin et al. (2004) *Biol. Reprod.* 70, 518-522). This observation further supports the functional importance of NOX5 and c-Abl in spermatozoa.

A recent report showed that the HV1 proton channel is likely to be responsible for cytoplasmic alkalinization in human spermatozoa, and that enhanced proton currents correlate with sperm capacitation and hypermotility (Lishko et al. (2010) *Cell* 140, 327-33729). The physiologic function of these channels has been characterized best in phagocytic leukocytes, where HV1-dependent H+ efflux compensates for the membrane depolarization and intracellular acidification generated by the electrogenic NADPH oxidase enzymatic activity (Morgan et al. (2009) *Proc. Natl. Acad. Sci. USA.* 106, 18022-18027; Ramsey et al. (2009) *Proc. Natl. Acad. Sci. USA* 106, 7642-7647; DeCoursey (2010) *Physiology* (Bethesda, Md.) 25, 27-40; El Chemaly et al. (2010) *J. Exp. Med.* 207. 129-S121-122).

The inventors found that the induction of superoxide production by $H_2O_2$ stimulated the motility of sperm cells. However, this effect was observed only in spermatozoa that were not already hyperactivated. The statistical analysis of sperm characteristics versus superoxide production confirmed experimental observation, establishing that pH and superoxide production were both important predictors of spermatozoa motility. The data showing a functional interaction between the HV1 proton channel and NOX5 NADPH oxidase, and the trends observed in statistical analysis, suggest strongly that the correlation between superoxide production and motility is pH dependent. Interestingly, the novel finding that progesterone, a proposed physiological sperm chemoattractant, is a modulator of the pH-dependent Ca2+ channel CatSper (Lishko et al. (2011) *Nature* 471, 387-391), provides a potential mechanism for linking Ca2+ entry, NOX5 activation, and ROS-stimulated hypermotility, thereby reinforcing the concept of a central role of NOX5 in human sperm motility.

Evidence is provided demonstrating NOX5 expression at the protein level and is functionally active in human spermatozoa. Moreover, the regulation of NOX5 by $H_2O_2$ is mediated by Ca2+ entry and c-Abl tyrosine kinase activation, while the downstream ROS generation is implicated in spermatozoa motility. Taken altogether, these results suggest that the expression levels and/or activities of NOX5, c-Abl, and HV1 are significant determinants of the redox status of human spermatozoa and consequently their motility and ovum-fertilizing potential. Moreover, NOX5 and the proteins regulating its activity represent new therapeutic targets for either male infertility (if NOX5 is hyperactive) or male contraception (if NOX5 is physiologically active).

II. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

NOX5 in Human Spermatozoa

NOX5 Expression in Human Spermatozoa.

Figure 1A:
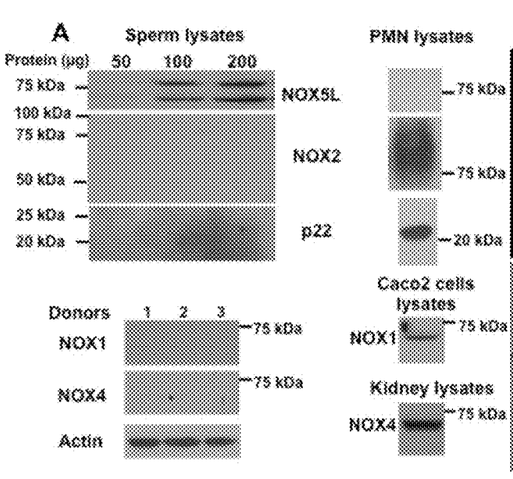
FIGS. 1A-1C. NOX5 expression in human spermatozoa. (A) Lysates from pooled human spermatozoa from several donors were analyzed by immunoblotting using antibody to either NOX2, p22 and NOX5 (upper panels) or NOX1 and NOX4 (lower panels). Comparisons were made using lysates from human neutrophils (PMN), CaCo2 cells, and mouse kidney as positive controls for NOX2, p22, NOX1 and NOX4, respectively. (B) Protein extracts of K562 cells stably transfected with a vector expressing either NOX5β☐ or Myc-tagged NOX5S were analyzed by immunoblot with antibody to either NOX5 or c-Myc. (C) Immunostaining of human spermatozoa with NOX5 antibody and CyTM 3-conjugated secondary antibody (top left and bottom right), nuclear staining with DAPI (top right and bottom right), and differential interference contrast (DIC) image (bottom left).

A lysate of pooled spermatozoa from several donors was used for immunoblot analysis with antibody specific for NOX5 or NOX2. The NOX5 antibody detected two main immunoreactive species with apparent molecular weights of ~80 and ~65 kDa (FIG. 1A), whereas no bands were observed using NOX2 antibody (FIG. 1A). Conversely, human neutrophil (PMN) lysates analyzed in parallel exhibited the presence of NOX2 but not NOX5. In addition, immunoblot analysis of sperm lysates using NOX1 or NOX4 antibody resulted in no detectable signals, whereas appropriate immunoreactive bands were detected in lysates of CaCo2 and kidney cells (FIG. 1A), which are known to express NOX1 and NOX4, respectively. These results suggest that the predominant NOX enzyme expressed in human spermatozoa is NOX5.

Figure 1B:
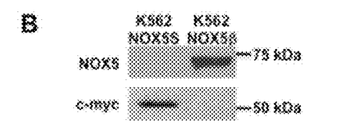

Since the NOX5 antibody was generated against a GST-peptide corresponding to the N-terminus of NOX5, including the EF-hand domains present in the long splice variants, such as NOX5β, it was possible that the antibody detected more than one long NOX5 variant. However, since the sequence of the peptide immunogen extended 10 amino acids into the predicted N-terminal domain of the short NOX5 variant, the more rapidly migrating band could have represented NOX5S. To test this possibility immunoblot analysis was performed using anti-NOX5 and anti-Myc on lysates of K562 cells stably over-expressing either NOX5β (El Jamali et al. (2008) Free Radic. Biol. Med. 44, 868-881) or Myc-tagged NOX5S. The data show that the NOX5 antibody recognized only NOX5β, while anti-Myc detected only Myc-NOX5S (FIG. 1B). Moreover, Myc-NOX5S exhibited an apparent molecular weight of ~55 kDa, which is substantially smaller than either of the bands detected in spermatozoa. It was concluded that the species recognized by anti-NOX5 in sperm lysates represent EF-hand-containing NOX5L splice variants. However, since their apparent molecular sizes do not match precisely to the NOX5β expressed in K562 cells, the exact sequences remain to be determined to identify the predominant NOX5L variants present in human spermatozoa.

Figure 1C:
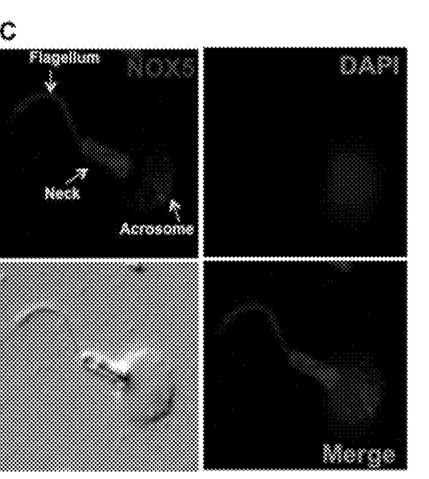

Immunostaining experiments confirmed the presence of NOX5 in human spermatozoa and showed its localization in the sperm flagellum, neck, and acrosome regions (FIG. 1C). These immunoblotting and immunostaining results together demonstrate for the first time that NOX5 is expressed in human spermatozoa.

Ca2+-Dependent Superoxide Production by Human Spermatozoa.

Figure 2A:
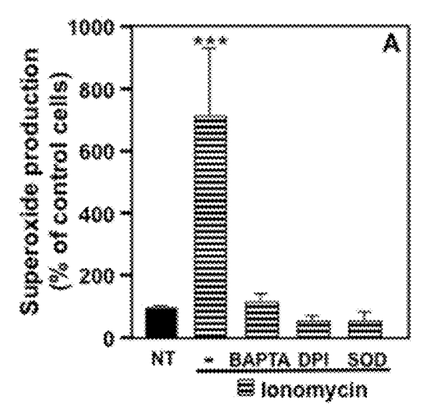
FIGS. 2A-2C. Spermatozoa produce superoxide in a Ca2+-dependent manner. Human spermatozoa were assayed for superoxide production using the luminol-based Diogenes reagent. Superoxide production was measured using whole sperm cells pre-incubated or not with various pharmacological agents [BAPTA (100 µM), DPI (10 µM), or SOD (400 U/ml)] and stimulated for 10 min with 1 µM ionomycin (A) or 1 µg/ml PMA (B). After normalization by subtraction of the zero-time value of the chemiluminescence output, the area under the curve was calculated as a measure of total superoxide production and was expressed as a percent of non-treated cells (NT). The data expressed are the means+/−SEM of 4-6 independent experiments. Asterisks indicate statistical significance versus control cells (NT). *P<0.001. (C) Dose-dependent effect of the NOX inhibitor GKT136901 on PMA-stimulated superoxide production by human neutrophils or spermatozoa. The data expressed are the means+/−SEM of 3-4 independent experiments. Asterisks indicate statistical significance versus neutrophil cells. *P<0.001.
Figure 2B:
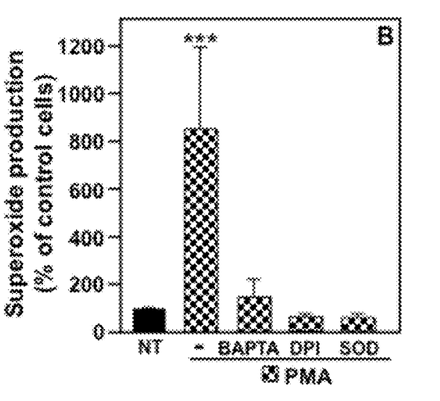

Since the binding of Ca2+ to N-terminal EF-hand domains activates NOX5L forms, the NOX5 function in human sperm was assessed by testing the ability of intact spermatozoa to produce superoxide upon exposure to the Ca2+ ionophore ionomycin (FIG. 2A). Using the superoxide-specific luminol-based Diogenes reagent chemiluminescence assay (El Jamali et al. (2008) Free Radic. Biol. Med. 44, 868-881), it was found that ionomycin induced vigorous superoxide production by human spermatozoa. The chemiluminescence signal detected was blocked by addition of superoxide dismutase (SOD), the flavoprotein oxidase inhibitor diphenylene iodonium (DPI), or the Ca2+ chelator BAPTA (FIG. 2A), indicating that under these conditions generation of superoxide anion by a Ca2+-dependent flavoprotein oxidase was being detected, such as NOX5. Similar patterns of superoxide generation and blocking agent effects were observed when spermatozoa were exposed to PMA (FIG. 2B), a potent phorbol ester activator of PKC that is known to regulate NOX5 activity (Jagnandan et al. (2007) J. Biol. Chem. 282, 6494-6507).

Figure 2C:
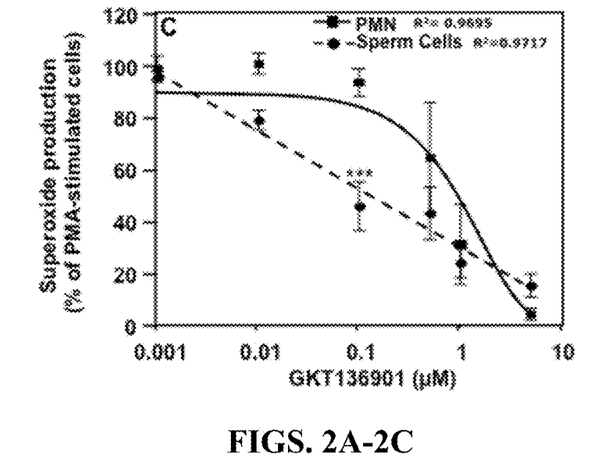

The effect of a newly described NOX inhibitor, GKT136901, was tested to further investigate whether NOX5 accounts for Ca2+-dependent superoxide production. This compound is a potent inhibitor of both NOX1 and NOX4 (Ki=160±10 nM and 165±5 nM, respectively) with a ~9-fold selectivity over NOX2 (Ki=1530±90 nM) (Laleu et al. (2010) J. Med. Chem. 53, 7715-7730; Sedeek et al. (2010) Am. J. Physiol. Renal. Physiol. 299, F1348-F1358). When tested under the same conditions as described by Laleu et al., GKT136901 showed an inhibitory constant of 450±10 nM for NOX5 (GenKyoTex, personal communication). The results show that in sperm cells, GKT136901 inhibited the stimulation of superoxide production by PMA in a concentration-dependent manner. GKT136901 was ~10-fold more potent in inhibiting superoxide production stimulated by PMA in sperm cells as compared with neutrophils (FIG. 2C). Since human spermatozoa do not express detectable levels of NOX1 or NOX4, these results strongly suggest that NOX5 protein expressed in human spermatozoa is the functionally active, superoxide-generating enzyme.

Effect of $H_2O_2$ on Superoxide Production by Human Spermatozoa.

Figure 3A:
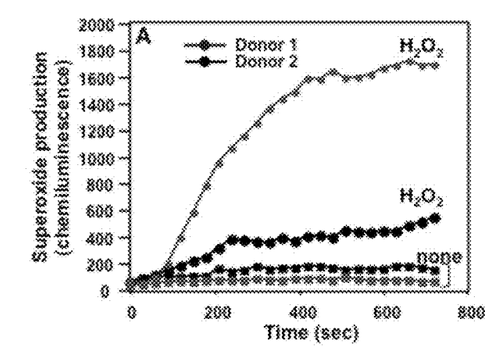
FIGS. 3A-3D. Dose- and time-dependent effects of H2O2 on superoxide generation by human spermatozoa. (A) Superoxide produced by spermatozoa from two different donors with or without 100 µM H2O2 was measured over the indicated time course. These results are representative of the range of superoxide responses observed among a total of 94 sperm donors. (B) Superoxide production was measured in sperm cells stimulated for 10 min with various concentrations of H2O2 (0-500 µM). (C) Superoxide production stimulated with 100 µM H2O2 was determined in sperm cells pre-incubated with BAPTA (100 µM), DPI (10 µM), SOD (400 U/ml), or GKT136901 (0.5 µM). Superoxide production was determined as in FIG. 2 and expressed as a percent of non-treated cells (NT). The data expressed in panels B and C are the means+/−SEM of 6-10 independent experiments. Asterisks indicate statistical significance versus control cells without H2O2. *P<0.05, P<0.01, *P<0.001 and hash sign indicate statistical significance versus cells stimulated with H2O2. #P<0.05, ##P<0.01, ###P<0.001. (D) Confocal images of spermatozoa incubated for 10 min without (NT) or with H2O2 were recorded using a Zeiss microscope. Each set of four photomicrograph panels corresponds to superoxide production (red fluorescence, top left), Ca2+ influx (green fluorescence, top right), the differential interference contrast (DIC) image (bottom left), and a merge picture of the two fluorescent images (bottom right). The scale bar indicates a size of 10 µm.
Figure 3B:
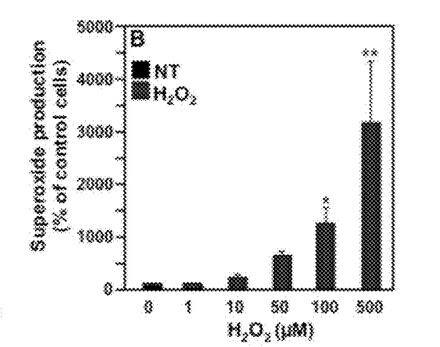
Figure 3C:
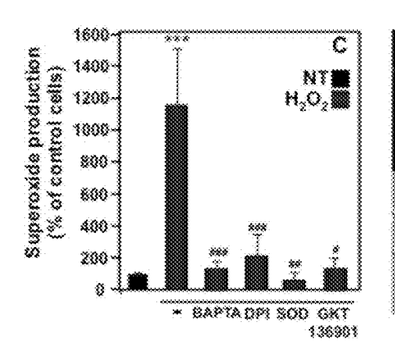

It has been previously demonstrated that exogenous $H_2O_2$ induces NOX5 activity in an over-expression system (El Jamali et al. (2008) Free Radic. Biol. Med. 44, 868-88124). Testing this regulation in human primary cells, it was found that $H_2O_2$ induced a marked burst in superoxide production by human spermatozoa, beginning within 1 to 2 min after peroxide addition and achieving maximal activity levels, varying somewhat among donors, in 5 to 10 min (FIG. 3A). The induction of superoxide generation was dose-dependent from 1 to 500 μM $H_2O_2$ (FIG. 3B). Subsequent experiments were performed using a standard concentration of 100 μM $H_2O_2$. As for superoxide generation induced by ionomycin or PMA, the chemiluminescence signal generated by exposure to $H_2O_2$ was nearly completely abrogated by the addition of SOD, BAPTA, DPI, or GKT136901 (FIG. 3C). Since superoxide production by phagocyte NOX2 is also regulated by $H_2O_2$, all semen samples in which leukocytes were evident by microscopic observation were discarded to ensure that leukocytes did not account for the superoxide signal stimulated by $H_2O_2$ in sperm samples.

Figure 3D:
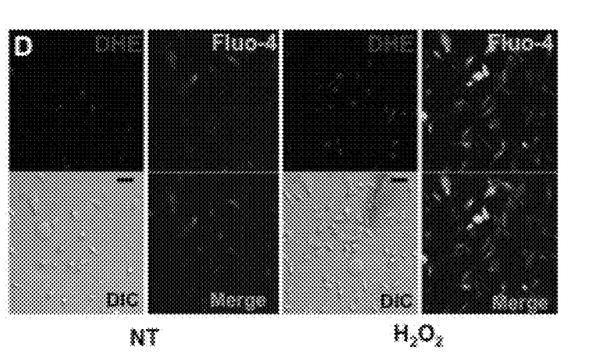

To confirm that spermatozoa produce superoxide when stimulated by $H_2O_2$, confocal images of spermatozoa freshly loaded with the red fluorescent superoxide probe dihydroethidine (DHE) were recorded. In addition, sperm cells were loaded with the Ca2+ indicator dye fluo4-AM to detect cytosolic Ca2+ responses in parallel with superoxide production. Spermatozoa exposed to $H_2O_2$ exhibited increases in cytosolic Ca2+ levels (green fluorescence), as well as the number and intensity of red-fluorescing cells, reflecting superoxide generation (FIG. 3D). Together with the chemiluminescence data (FIG. 3A, 3B, 3C), these confocal imaging results strongly suggest that the superoxide production induced by $H_2O_2$ was due to Ca2+-mediated activation of the NOX5 splice variants expressed in human spermatozoa. The partial co-localization of Ca2+ influx and superoxide production suggests partial temporal overlap of these events, as previously found in NOX5 over-expression studies (El Jamali et al. (2008) Free Radic. Biol. Med. 44, 868-881).

Role of c-Abl in $H_2O_2$-Induced Sperm Superoxide Production.

Figure 4A:
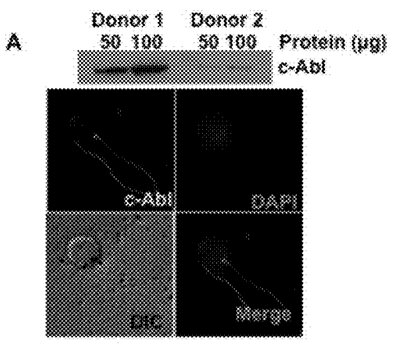
FIGS. 4A-4D. Role of c-Abl in the activation of NOX5 by H2O2. (A) Above is an immunoblot analysis using a c-Abl antibody on human spermatozoa from two different donors. Below is immunostaining of human spermatozoa with c-Abl antibody and FITC-conjugated secondary antibody (top left and bottom right), nuclear staining with DAPI (top right and bottom right), and the DIC image (bottom left). (B) Immunostaining of human spermatozoa with c-Abl antibody as in panel A (top left and top right) and NOX5 antibody and CyTM 3-conjugated secondary antibody (top left and bottom left), and the DIC image (bottom right). Note colocalization in the top left panels. The scale bar indicates a size of 5 µm. (C) Immunoblot analysis (above) and immunostaining (below, right panels) using phospho-c-Abl antibody were performed on human spermatozoa incubated for 10 min with or without (NT) 100 µM H2O2. DIC images (left panels) and DAPI nuclear staining (middle panels) are also shown. (D) Superoxide production was determined in sperm cells pre-incubated for 1 h with 50 µM imatinib and then stimulated for 10 min with 100 µM H2O2. Superoxide production was determined as in FIG. 2 and expressed as a percent of non-treated cells (NT). The data expressed are the means+/−SEM of 4 independent experiments. Asterisks indicate statistical significance versus control cells without H2O2. ***P<0.001. Hash sign indicates statistical significance versus cells stimulated with H2O2. #P<0.05.
Figure 4B:
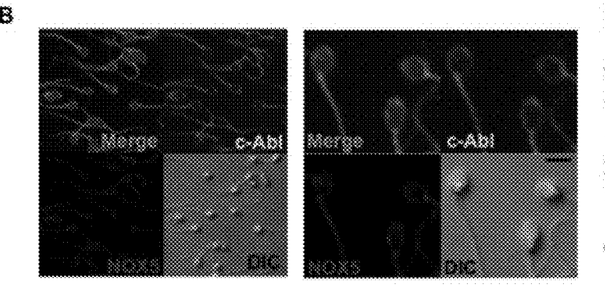
Figure 4C:
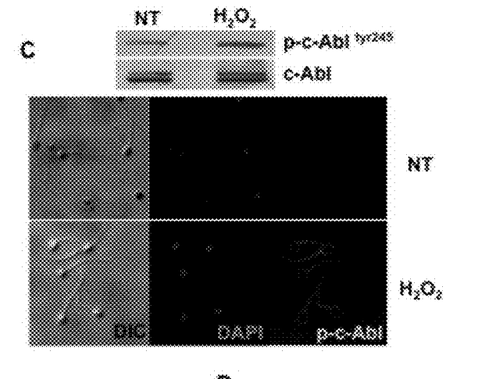
Figure 4D:
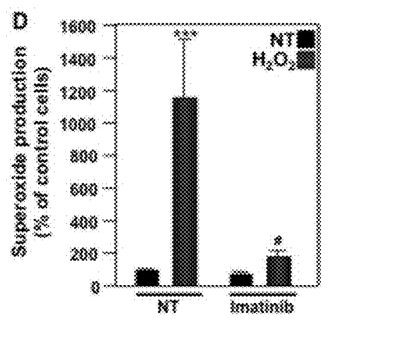

It has been shown previously that c-Abl tyrosine kinase plays a central role in the induction of NOX5 activity in response to $H_2O_2$ (El Jamali et al. (2008) Free Radic. Biol. Med. 44, 868-881). To investigate the potential role of c-Abl in primary human spermatozoa, NOX5 expression and regulation by $H_2O_2$ was assessed. Immunoblot analysis showed that c-Abl was expressed in spermatozoa (FIG. 4A). Immunostaining demonstrated the presence of c-Abl in the flagellum, neck, and acrosome regions, as well as co-localization with NOX5, as assessed by double immunostaining (FIG. 4B). Stimulation of spermatozoa by $H_2O_2$ induced the phosphorylation of c-Abl on tyrosine 245, an indication of its activation (FIG. 4C), as demonstrated by both immunoblot and immunostaining. Pretreatment of human spermatozoa with the selective c-Abl inhibitor imatinib mesylate significantly decreased superoxide production induced by $H_2O_2$ (FIG. 4D). These results suggest that $H_2O_2$—NOX5 regulation in human spermatozoa is mediated through a c-Abl-dependent signaling pathway.

Superoxide Production by NOX5 Requires HV1 Proton Channel.

It has been recently reported that HV1 voltage-regulated proton channels present in human spermatozoa are implicated in their motility (Lishko et al. (2010) *Cell* 140, 327-337). Since HV1-dependent proton efflux has been shown to compensate membrane depolarization and intracellular acidification arising from phagocyte NOX2 enzymatic activity (Morgan et al. (2009) *Proc. Natl. Acad. Sci. USA.* 106, 18022-18027; Ramsey et al. (2009) *Proc. Natl. Acad. Sci. USA* 106, 7642-7647; DeCoursey (2010) *Physiology* (Bethesda, Md.) 25, 27-40; El Chemaly (2010) *J. Exp. Med.* 207. 129-S121-122), it was hypothesized that the activity of this channel is associated with NOX5-dependent superoxide production in human spermatozoa.

Figures 5A, 5B, 5C, 5D:
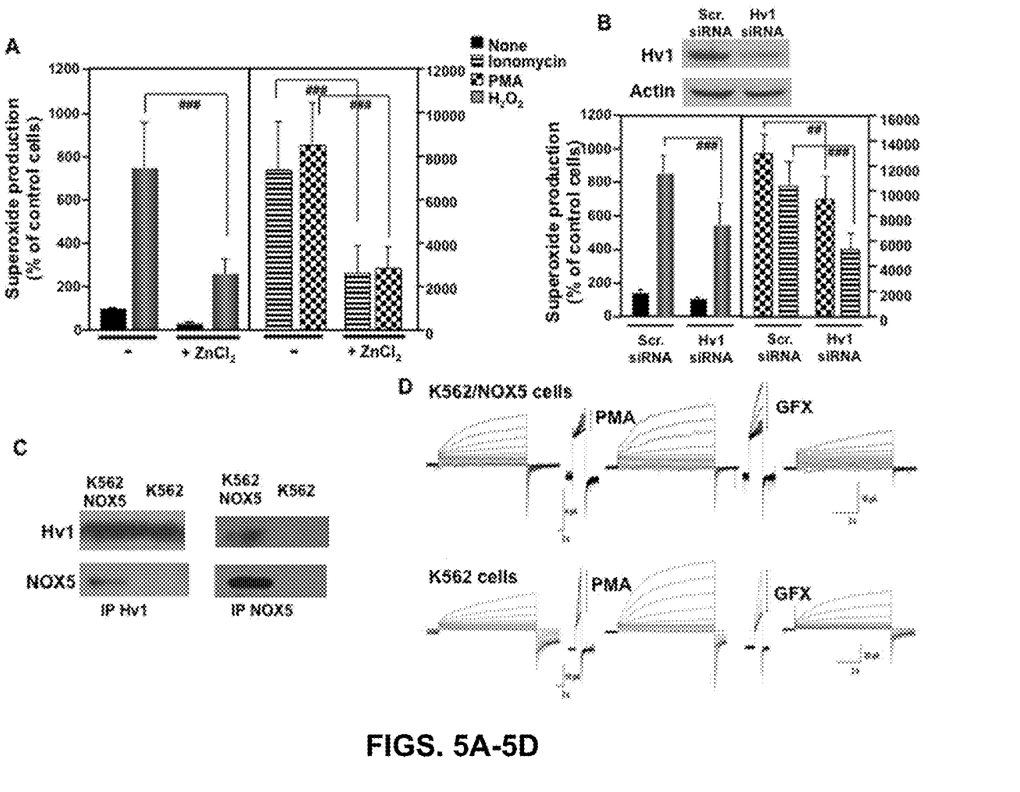

The potential interaction of NOX5 and HV1 was investigated using K562 cells over-expressing NOX5β. The impact of HV1 function on NOX5 activity was evaluated using Zn2+, a potent inhibitor of HV1 proton currents (Musset et al. (2008) *J. Physiol.* 586, 2477-248634), or siRNA to down-regulate the expression of HV1. It was observed that induction of superoxide production in K562/NOX5 cells stimulated by ionomycin, PMA, or $H_2O_2$ was decreased by 1 mM $ZnCl_2$ (FIG. 5A) or by HV1 siRNA (FIG. 5B), by 50-70% or 30%-50%, respectively. Furthermore, immunoprecipitation experiments showed the presence of NOX5 protein in HV1-immunoprecipitates and HV1 protein in NOX5-immunoprecipitates from lysates of K562/NOX5 cells, but not control K562 cells (FIG. 5C). These results suggest the existence of a specific interaction between HV1 and NOX5 proteins.

Proton currents were consistently recorded in both K562 cells (4 of 5 patched cells) and K562/NOX5 cells (12 of 14 cells) voltage-clamped in a perforated-patch configuration (FIG. 5D) (DeCoursey et al. (2000) *Proc. Natl. Acad. Sci. USA.* 97, 6885-6889). The current density (i.e., current/membrane area) at 40, 50, 60, and 70 mV was larger in K562 cells than in K562/NOX5 cells by a factor of 1.30 on average, although these differences were not statistically significant. The proton channels responded to PMA stimulation with a characteristic array of changes in their behavioral properties, designated "enhanced gating mode" (negative shift of the gH-V relationship, faster activation, slower deactivation, increased gH,max) (DeCoursey et al. (2000) *Proc. Natl. Acad. Sci. USA.* 97, 6885-6889; Banfi et al. (1999) *J. Exp. Med.* 190, 183-194; Banfi et al. (2000) *Science* (New York, N.Y.) 287, 138-142). Most features of the PMA response of proton channels were reversed by the addition of the PKC inhibitor GFX (FIG. 5D) (Musset et al. (2008) *J. Physiol.* 586, 2477-2486; Morgan et al. (2007) *J. Physiol.* 579, 327-344). These data demonstrate that both K562 cells and K562/NOX5 cells expressed functional proton channels with the characteristic features of HV1. Collectively, the data in K562 and K562/NOX5 cells demonstrate that a functional interaction exists between HV1 and NOX5, wherein HV1 is required for sustaining NOX5-dependent superoxide production.

Figures 6A, 6B:
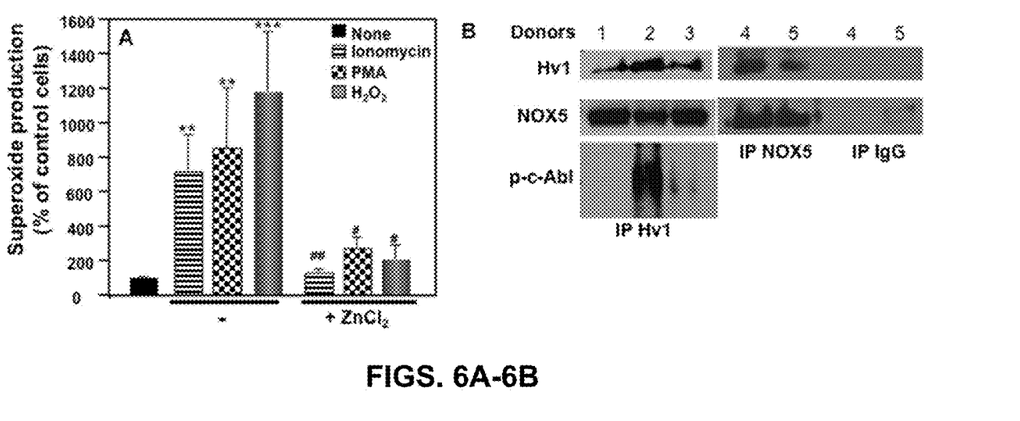
FIGS. 6A-6B. Hv1 activity affects NOX5-dependent superoxide production in human spermatozoa. (A) Superoxide production by spermatozoa pre-incubated for 5 min with or without 1 mM ZnCl2 and then stimulated with ionomycin (1 µM), PMA (1 µg/ml), or H2O2 (100 µM) was measured and expressed as in FIG. 2. The data expressed are the means+/−SEM of 4-6 independent experiments. Asterisks indicate statistical significance versus control cells without stimulus. P<0.01; *P<0.001. The hash signs indicate statistical significance versus stimulated cells in the absence of ZnCl2. ##P<0.01; ###P<0.001. (B) Immunoprecipitation of NOX5 or HV1 protein was performed using total protein lysates isolated from sperm cells of different donors. Non-immune IgG was used to control for specificity. The content of the immunoprecipitates was analyzed by immunoblot using HV1, NOX5, and phospho-c-Abl antibodies.

Similar to the K562/NOX5 cell studies, it was found, in human spermatozoa that superoxide production induced by $H_2O_2$, PMA, or ionomycin was Zn2+-sensitive (FIG. 6A) and that HV1 co-immunoprecipitated with NOX5, when the immunoprecipitation was performed with either HV1 or NOX5 antibodies (FIG. 6B). Interestingly, the activated form of c-Abl (p-c-$Abl^{tyr245}$) implicated in NOX5 regulation, was also detected in HV1 immunopreciptates (FIG. 6B), suggesting the existence of a tri-molecular complex comprising HV1, NOX5, and activated c-Abl. Taken together, these results provide strong evidence for a functional interaction between HV1 and NOX5 in human spermatozoa.

Effect of $H_2O_2$ on Sperm Motility.

Figure 7A:
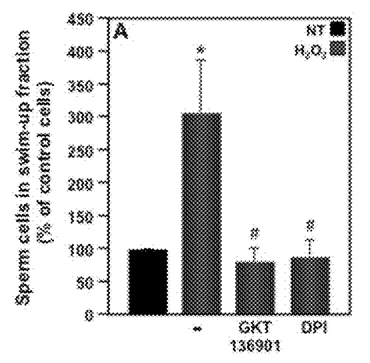
FIGS. 7A-7C. Effect of H2O2 on sperm motility. (A) From each donor, 2X107 spermatozoa pre-incubated or not with GKT136901 (0.5 µM) or DPI (10 µM) were incubated without (NT) or with 100 µM H2O2 for 10 min and then subjected to the swim-up procedure. The number of spermatozoa present in the upper fraction was determined and expressed as a percent of NT samples. The data expressed are the means+/−SEM of 10 independent experiments. Asterisks indicate statistical significance versus control cells without H2O2. *P<0.05. Hash signs indicate statistical significance versus H2O2-stimulated cells. #P<0.05. (B) The effect of H2O2 on superoxide production by spermatozoa before the swim-up procedure and by spermatozoa collected from the upper fraction after the swim-up procedure was determined as in FIG. 3. The data represent the percent increase in H2O2-induced superoxide formation and are the means+/−SEM of 4 independent experiments. Hash sign indicates significance versus sperm cells tested before the swim up procedure. #P<0.05. (C) Hypothetical scheme for the interaction of NOX5 with the HV1 channel implicated in human spermatozoa hypermotility.

Since low levels of $H_2O_2$ can induce sperm capacitation (Aitken et al. (2004) *Free Radic. Biol. Med.* 36, 994-1010; Aitken and Vernet (1998) *J. Reprod. Fertil. Suppl.* 53, 109-118; De Lamirande and O'Flaherty (2008) *Biochim. Biophys. Acta.* 1784, 106-115) and because HV1 interacts with NOX5, the effect of $H_2O_2$ on sperm cell motility was tested. Sperm cells were incubated with or without 100 μM $H_2O_2$ for 10 min and then motile spermatozoa were collected following the swim-up procedure. The incubation of spermatozoa with $H_2O_2$ resulted in an increase in the number of sperm in the swim-up fraction (FIG. 7A), suggesting that $H_2O_2$ enhanced spermatozoa motility. To investigate whether the effect of $H_2O_2$ on motility was due to NOX5, the swim-up experiment was performed in the presence of NOX inhibitors. When spermatozoa were pre-incubated with DPI or GKT136901, the effect of $H_2O_2$ on motility was abrogated. These results strongly suggest that the induction of spermatozoa motility by $H_2O_2$ is dependent on NOX5 activity.

Figure 7B:
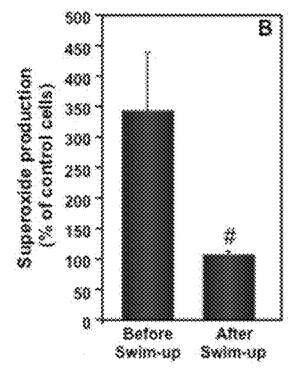
Figure 7C:
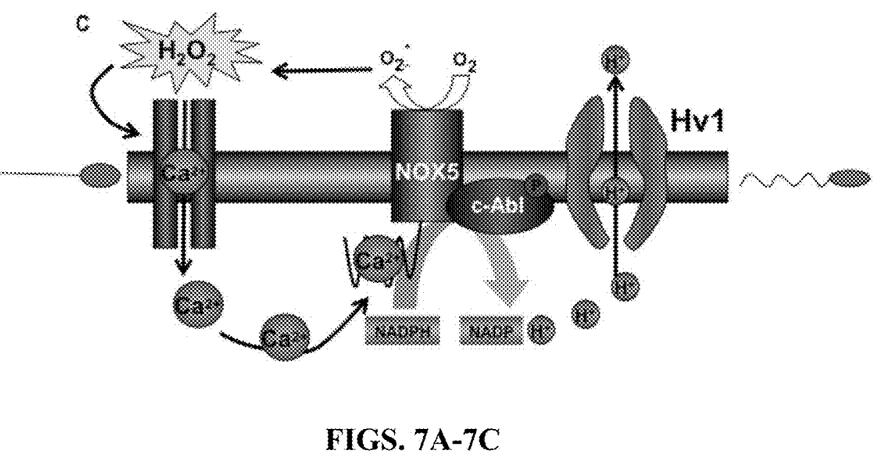
Figure 8:
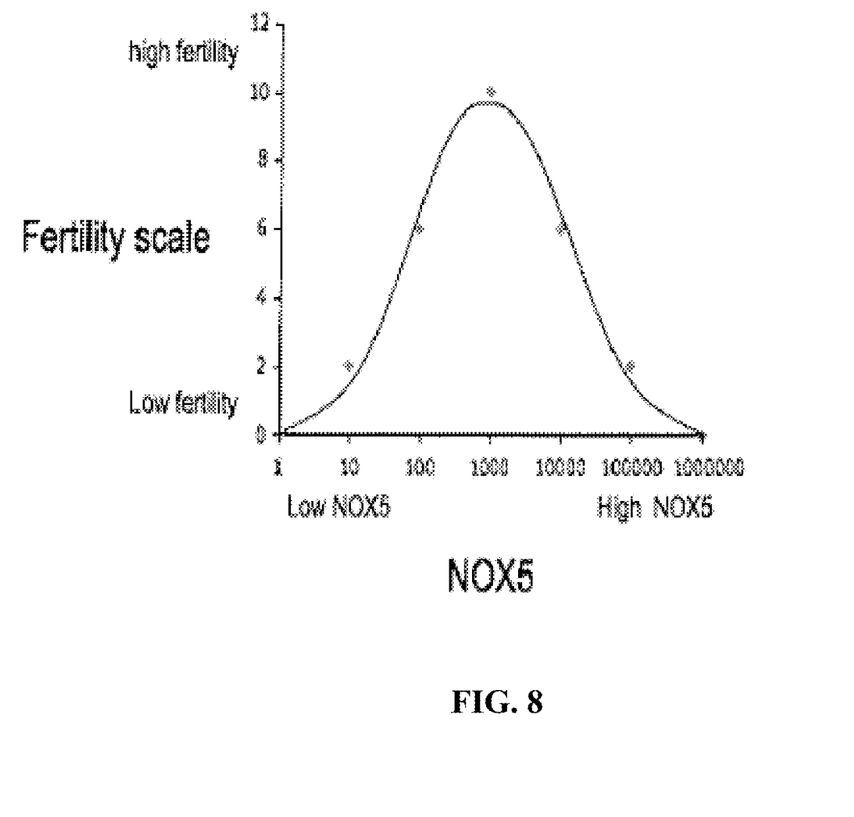
FIG. 8. An illustration of fertility versus NOX5 levels.

It was observed that the effect of $H_2O_2$ on motility was especially prominent in semen samples that had the lowest baseline percentages of motile sperm. In addition, when superoxide production was measured using spermatozoa collected from the upper fraction after the spontaneous (i.e., without $H_2O_2$) swim-up procedure, these hypermotile spermatozoa did not produce superoxide when stimulated by $H_2O_2$ compared with pre-swim-up cells (FIG. 7B). This finding indicated that following the hyperactivation process spermatozoa are no longer responsive to $H_2O_2$.

Semen pH-Dependent Correlation Between Superoxide Production and Sperm Motility.

Sperm samples (n=128) were assessed according to the World Health Organization (WHO) laboratory manual (World Health Organization, and Department of Reproductive Health and Research. (2010) WHO ISBN 978 92 4 154778 941) for the examination and processing of human semen. Abstinence, defined as the number of days since the previous ejaculation, ranged from 1 to 14 days and was significantly associated with sperm concentration (r=0.28. P=0.001), total sperm cell count (r=0.27, P=0.002), number of motile sperm cells (r=0.24, P=0.005), and concentration of immature forms (r=0.32, P<0.001) (data not shown).

It is known that pH increases during capacitation Neri-Vidaurri et al. (2006) *Biochem. Biophys. Res. Commun.* 343, 105-109; Garcia and Meizel (1999) *Mol. Reprod. Dev.* 52, 189-195; Zeng et al. (1996) *Dev. Biol.* 173, 510-520; Florman et al. (2010) *Cell* 140, 310-312). Considering the relationship between HV1, an important regulator of pH in human spermatozoa, and NOX5, sperm characteristics as a function of semen pH were analyzed (Table 1), which was categorized into three levels (<8, 8-8.5, >8.5) for these analyses. Significant differences were found between pH levels for semen viscosity (P=0.02), total sperm count (P=0.04), total number of motile sperm (P=0.02), percent of motile sperm (P=0.009), and sperm progressive motility (progression), which is defined as spermatozoa moving actively, either linearly or in a large circle (P=0.04). Progression was described according to WHO manual using an ordered categorical scale from 1 to 4, where a higher number indicates a higher progressive motility (World Health Organization, and Department of Reproductive Health and Research. (2010) WHO ISBN 978 92 4 154778 9). Superoxide production did not vary significantly with semen pH. It was observed that a significant difference in basal superoxide production was associated with higher levels of sperm progression (≤2, 3, >3) (P=0.02). However, superoxide production stimulated by $H_2O_2$ or PMA were not significantly associated with progression (data not shown).

A regression model was built to analyze for possible correlations among semen pH, sperm motility, and superoxide production, adjusting for abstinence and pH. There appears to be a nonlinear association (inverted U function) between pH and a number of sperm metrics, so pH levels were re-categorized into levels more conducive to sperm activity (8.0-8.5) and those less conducive to sperm activity (<8 or >8.5) for our regression analyses. The regression model (Table 2) confirmed the previous observations (Table 1), since significant increases in sperm progressive motility (OR=3.38, 95% CI: 1.25 to 9.15, P=0.02) and percent of motile sperm (mean difference=14, 95% CI: 4 to 23, P=0.004) were observed for the pH 8.0-8.5 group, compared with the group with either high or low pH values that are less conducive to sperm activity (Table 2). Basal and stimulated ($H_2O_2$ or PMA) levels of superoxide production tended to be higher in the pH 8.0-8.5 group relative to the pH<8 or >8.5 group, although these associations were not significant (P=0.11, 0.29, 0.18 for superoxide production measured under basal condition or stimulated by $H_2O_2$ or PMA, respectively). Because of the small number of sperm samples in the low plus high pH group, the analysis of sperm motility and superoxide production was conducted only for the median pH group (8.0-8.5). There was a significant correlation between the percent of motile sperm and basal level of superoxide production. While increased superoxide production stimulated by PMA or $H_2O_2$ was significantly associated with higher progression ($H_2O_2$-stimulated superoxide production: OR=1.22, 95% CI: 1.0 to 1.5, P=0.05; PMA-stimulated superoxide production: OR=1.21, 95% CI: 1.01 to 1.45, P=0.04). These analyses demonstrate that semen pH and sperm superoxide production are closely associated with sperm motility and suggest that the correlation between superoxide production and sperm motility is pH-dependent.

TABLE 1

Semen analysis parameters and superoxide production as a function of semen pH (<8. 8-8.5,

|  | pH <8 (n = 5) Mean ± SD [median] | pH: 8-8.5 (n = 107) Mean ± SD [median] | pH >8.5 (n = 16) Mean ± SD [median] | P-value[1] |
|---|---|---|---|---|
| Basal superoxide Production (AUC)[3] | 911 ± 1040 [559] | 11100 ± 49100 [486] | 2240 ± 6700 [227] | 0.09 |
| $H_2O_2$ stimulated superoxide Production (AUC)[4] | 5030 ± 8870 [1226] | 30200 ± 80300 [1768] | 6160 ± 10600 [911] | 0.55 |
| PMA-stimulated superoxide Production (AUC)[5] | 9790 ± 15900 [2487] | 176000 ± 526000 [4603] | 54300 ± 145000 [2241] | 0.67 |
| Concentration ($10^6$/ml) | 78.9 ± 65.2 [89] | 93.1 ± 81.1 [76.2] | 45.1 ± 44.9 [21.9] | 0.05 |
| Total sperm cell count ($10^6$) | 292.2 ± 311.7 [230] | 249.4 ± 240.7 [182.3] | 126.5 ± 188.6 [38.7] | 0.04 |
| Percent of motile sperm | 48 ± 28 [60] | 52 ± 19 [60] | 36 ± 20 [40] | 0.009 |
| Total number of motile sperm ($10^6$) | 168.7 ± 183.6 [138] | 137.8 ± 140.3 [99.7] | 65.2 ± 120.1 [19.3] | 0.02 |
| Morphology (% Normal)[6] | 29 ± 17 [37] | 30.2 ± 17.5 [29.5] | 25.3 ± 18.5 [25] | 0.51 |
| Immature Forms ($10^6$/ml) | 2.4 ± 3.9 [0] | 2.9 ± 5.7 [0] | 1.2 ± 2.4 [0] | 0.64 |
|  |  |  |  | P-value[2] |
| Progression, n (%) |  |  |  | 0.04 |
| ≤2 | 4 [80] | 37 [35] | 10 [62] |  |
| 3 | 0 [0] | 48 [45] | 5 [31] |  |
| >3 | 1 [20] | 22 [21] | 1 [6] |  |
| Viscosity[7], n (%) |  |  |  | 0.02 |
| 0 | 5 [100] | 88 184| | 9 [56] |  |
| >0 | 0 10] | 17 [16] | 7 [44] |  |
| Agglutination[8], n (%) |  |  |  | 0.33 |
| 0 | 3 [60] | 53 [50] | 5 [31] |  |
| >0 | 2 [40] | 53 [50] | 11 [69] |  |

[1]Kruskal-Wallis test
[2]Fisher's exact test
[3]Missing 25 for pH 8-8.5, 4 for pH >8.5
[4]Missing 30 for pH 8-8.5, 4 for pH >8.5
[5]Missing 38 for pH 8-8.5, 4 for pH >8.5
[6]Missing 1 for pH 8-8.5
[7]Missing 2 for pH 8-8.5
[8]Missing 1 for pH 8-8.5

TABLE 2

Odd ratio or mean differences of sperm motility and superoxide production for pH 8-8.5 versus pH <8 & >8.5

|  | pH 8-8.5 vs. pH <8 & >8.5 | |
|---|---|---|
| Outcome | Odd ratio (95% CI) | P-value[1] |
| Progression[2] | 3.38 (1.25, 9.15) | 0.02 |
|  | Mean Difference (95% CI) | P-value[3] |
| Log Total number of sperm | 0.85 (0, 1.7) | 0.05 |
| Percent of motile sperm | 13.90 (4.4, 23.3) | 0.004 |

TABLE 2-continued

Odd ratio or mean differences of sperm motility and superoxide production for pH 8-8.5 versus pH <8 & >8.5

| | | |
|---|---|---|
| Log Total number of motile sperm | 0.91 (0.09, 1.72) | 0.03 |
| Log Basal superoxide production | 0.97 (−0.22, 2.16) | 0.11 |
| Log $H_2O_2$ stimulated superoxide production | 0.64 (−0.55, 1.84) | 0.29 |
| Log PMA-stimulated superoxide production | 1.00 (−0.48, 2.47) | 0.18 |

[1]Ordinal logistic regression
[2]Progression is a 3-level categorical variable (≤2, 3, >3)
[3]Linear regression of each sperm characteristic in terms of pH with an adjustment for log abstinence

TABLE 3

Association between superoxide production and progression or percent of motile sperm for pH 8-8.5[1]

| Predictor | Progression | | Percent of motile sperm | |
|---|---|---|---|---|
| | Odds Ratio (95% CI) | P value[2] | Mean diff (95% CI) | P value[3] |
| Log Basal superoxide production (n = 82) | 1.19 (0.98-1.45) | 0.08 | 1.57 (0.05-3.08) | 0.04[4] |
| Log $H_2O_2$ stimulated superoxide production (n = 77) | 1.22 (1-1.5) | 0.05[4] | 0.35 (−1.02-1.72) | 0.61 |
| Log PMA-stimulated superoxide production (n = 69) | 1.21 (1.01-1.45) | 0.04[4] | 0.89 (−0.43-2.21) | 0.19 |

[1]Analysis was performed among those with pH levels 8-8.5 (N = 107)
[2]Ordinal logistic regression of progression in terms of each measure of superoxide production with an adjustment for log abstinence
[3]Linear regression of percent of motile sperm in terms of each measure of superoxide production with an adjustment for log abstinence Procedures Semen Samples and Sperm Isolation.

Human semen samples were obtained from patient donors as a part of their clinical evaluation for fertility and reproductive health status. Portions of the samples not required for clinical analyses were de-identified and made available for the research protocols described. Under these conditions, the Institutional Review Board determined that the study is exempt from requirements for protocol approval and informed consent. Semen was collected by masturbation into sterile plastic containers and allowed to liquefy for at least 30 min before being processed. The samples were centrifuged (500 g, 15 min) to separate the seminal plasma from spermatozoa, and the pellet washed twice in phosphate-buffered normal saline pH 7 with 10 mM glucose (PBS-G). The spermatozoa were then counted in a hemocytometer chamber, resuspended in PBS-G at $10^9$/ml, and used for superoxide assays. Sperm samples containing leukocytes detected by microscopic examination were excluded from the study. For selected experiments, motile spermatozoa were collected using the swim-up procedure (Vijayakumar et al. (1986) *Arch. Androl.* 17, 223-230; Parrish and Foote (1987) *J. Androl.* 8, 259-266). Briefly, the spermatozoa were sedimented by centrifugation (500 g, 15 min) and the tube was then incubated upright for 60 min at 37° C. Motile spermatozoa that progressed from the pellet into the supernatant (swim-up fraction) were collected by aspiration and counted.

Immunoblot Analysis.

Spermatozoa resuspended in lysis buffer A (20 mM HEPES, pH 7.9; 350 mM NaCl; 0.5 mM EDTA; 0.5 mM EGTA; 1 mM MgCl2; 10% glycerol (v/v); 1% Nonidet P-40 (v/v); 10 mM NaF; 0.1 mM $Na_3VO_4$ [orthovanadate], 8 mM β-glycerophosphate; phosphatase inhibitor cocktail I and II [Sigma]; and protease inhibitor cocktail [Roche, Mannheim, Germany]) were sonicated 3 times for 5 sec each (20 watts). Lysates were cleared by centrifugation (10,000 g, 15 min). Aliquots containing 60-200 µg of protein were separated on 4-20% SDS polyacrylamide gradient gels and transferred to polyvinylidene difluoride (PVDF) membranes. The filters were incubated with antibodies directed against c-Abl (Sigma, St. Louis, Mo. clone Abl-148 cat#A5844), phosphotyrosine 245 c-Abl (Cell Signaling, Danvers, Mass. cat#2861), NOX5 (kindly provided by William Nauseef, University of Iowa) (El Jamali et al. (2008) *Free Radic. Biol. Med.* 44, 868-881), NOX2 (kindly provided by Mark Quinn, Montana State University), NOX4 (Santa Cruz Biotechnology, Santa Cruz, Calif., cat# sc-301141) or NOX1 (GeneTex, Irvine, Calif. cat# GTX-103888), p22-phox (Santa Cruz Biotechnology, cat#sc-20781), c-Myc (Santa Cruz Biotechnology, cat# sc-40). Immunoblotting with HV1 antibody was performed using an affinity-purified polyclonal antibody that recognizes the intracellular N-terminal domain of the human HV1 protein (Petheo et al. (2010) *PloS. One.* 5, e14081). Immunoblots using actin antibody (Sigma, cat# A2066) were used to control for loading. The antigen-antibody complexes were visualized by enhanced chemiluminescence (ECL, Amersham, Pittsburgh, Pa.).

Immunoprecipitation.

Total protein extracts of either K562, K562/NOX5, or human sperm cells prepared in buffer A (250 µg of protein) were pre-cleared with rabbit IgG (Sigma) and protein A/G-agarose (Santa Cruz Biotechnology), incubated overnight with anti-NOX5, anti-HV1 or non-specific IgG antibody as a negative control, and precipitated with protein A/G-agarose for an additional 3 h. The immune complexes were washed with lysis buffer, separated on 4-20% SDS-polyacrylamide gradient gels, and transferred to PVDF membranes. The filters were incubated with either anti-NOX5, anti-HV1 or anti-phosphotyrosine 245 c-Abl antibodies. The antigen-antibody complexes were visualized by enhanced chemiluminescence (ECL, Amersham, Pittsburgh, Pa.).

Immunostaining.

For immunohistological analyses, a drop of spermatozoa suspended in PBS-G was placed on a poly-L-lysine-coated glass slide, fixed in 4% (w/v) paraformaldehyde and permeabilized with 0.1% Triton X-100 (v/v) for 15 min at 4° C. Spermatozoa were then subjected to immunostaining using the antibodies described above against NOX5, c-Abl, and phospho-Tyr-245-c-Abl along with CyTM 3- or FITC-conjugated secondary antibody (Zymed, San Francisco, Calif.). Protein expression was visualized on a fluorescence microscope (Zeiss, Thornwood, N.Y.). For negative controls, cells were incubated with isotype-matched control antibodies with no known specificity.

Superoxide Assay.

Superoxide generation was measured using a luminol-based chemiluminescence assay (Diogenes reagent, National Diagnostics, Atlanta, Ga.). The specificity of this assay for superoxide vs. $H_2O_2$ was previously demonstrated (El Jamali et al. (2008) *Free Radic. Biol. Med.* 44, 868-881). Spermatozoa were suspended at $10^9$/ml in PBS-G. A 100 µl aliquot of the Diogenes reagent was mixed with $2\times10^7$ spermatozoa and incubated at 37° C. for 2-4 minutes. Superoxide generation was measured at baseline and after stimulation with ionomycin (1 µM), phorbol myristate acetate (PMA, 1 µg/ml), or $H_2O_2$ (100 µM and other concentrations as indicated). Chemiluminescence was measured every 30-60 sec for up to 10-15 min using a Clarity™ BioTek luminometer and an integration time of 5 sec.

Pharmacologic Inhibitors.

Spermatozoa were pre-incubated for 5 min prior to the superoxide assay with 400 U/ml superoxide dismutase (SOD), 10 µM diphenylene iodonium (DPI), or 100 µM 1,2-Bis (2-aminophenoxy) ethane-N,N,N',N'-tetraacetic acid (BAPTA). A pre-incubation time of 1 h was used for the tyrosine kinase inhibitor imatinib mesylate (50 µM, Novartis Pharma AG, Basel, Switzerland). In some experiments, cells were pre-exposed to the NOX inhibitor 2-(2-chlorophenyl)-4-methyl-5-(pyridin-2-ylmethyl)-1H-pyrazolo[4,3-c]pyridine-3,6(2H,5H)-dione (GKT136901, 0.5 µM and other concentrations as indicated) for 10 min before exposure to either $H_2O_2$ or PMA. GKT136901 (GenKyoTex SA, Geneva, Switzerland) is a drug-like small molecule with high affinity and specificity for NOX1 and NOX4 (Laleu et al. (2010) *J. Med. Chem.* 53, 7715-7730; Sedeek et al. (2010) *Am. J. Physiol. Renal. Physiol.* 299, F1348-F1358) and to a lesser extent for NOX5.

Live Cell Imaging.

Spermatozoa suspended in PBS-G were plated on poly-L-lysine-coated glass coverslips ($2\times10^5$ cells/ml) in PBS-G and loaded with 6 µM fluo4-AM and 300 nM dihydroethidine (DHE) (Molecular Probes, Carlsbad, Calif.) 10 min before imaging. Ca2+ influx and superoxide production were recorded using a confocal microscope (LSM 510; Carl Zeiss MicroImaging, Inc., Thornwood, N.Y.) with a 63×/1.4 NA plan-apochromat objective. Fluo-4 and DHE fluorescence emissions were excited with dual laser at 488/543 nm attenuated to avoid photobleaching and saturation. Detection was through a 545 nm long-pass dichroic mirror and a band-pass filter at 500-530 for fluo-4 and LP560 for DHE.

Cell Culture and Down-Regulation of HV1 Protein by siRNA.

Human leukemia cells stably transfected with an empty vector (K562 cells) or a vector encoding for NOX5 (K562/NOX5) were grown in RPMI medium supplemented with 10% (v/v) fetal bovine serum, plus 100 U/ml penicillin and 100 µg/ml streptomycin and the appropriate selection antibiotic. Cells in the logarithmic phase of growth were transfected with a mix of HV1 siRNA (Sigma) or with scrambled siRNA (Sigma) using the Neon system (Invitrogen, Carlsbad, Calif.) according to the manufacturer's recommendations. Cells were tested 48 h after transfection for superoxide production and the down-regulation of HV1 protein was detected by immunoblot using the affinity-purified rabbit polyclonal HV1 antibody raised against an N-terminal domain of HV1 human protein (Petheo et al. (2010) *PloS. One.* 5, e14081).

Patch Clamp Analysis.

Micropipettes were pulled in several stages using a Flaming-Brown automatic pipette puller (Sutter Instruments, San Rafael, Calif.) from 7052 glass (Garner Glass Co., Claremont, Calif., USA), coated with Sylgard 184 (Dow Corning Corp., Midland, Mich.), heat polished to a tip resistance between 2 and 10 MΩ. Electrical contact with the pipette solution was achieved using a chloride silver wire. The reference electrode was made from an Ag—AgCl wire connected to the bath through an agar bridge made with Ringer solution (160 mM NaCl, 4.5 mM KCl, 2 mM $CaCl_2$, 1 mM $MgCl_2$, 5 mM Hepes adjusted to pH 7.4). Current signal from the Axopatch 200B (Axon Instruments, Foster City, Calif.) was recorded on PC through a Lab View SCB-68 (National Instruments, Austin, Tex.). Further data analysis was made with Origin 7.5. Seals were formed in Ringer solution in the bath, and the potential was zeroed when the pipette was in contact with the cell. Most measurements were done between 21 and 25° C.

K562 cells were transferred on chips or pipette into the recording chamber. To leave internal signaling pathways undisturbed, the perforated patch configuration was used. Low access resistance was usually reached after 5-10 minutes. The perforated patch recording bath and pipette solution contained 50 mM $NH^{4+}$ in the form of $(NH_4)_2SO_4$, 2 mM $MgCl_2$, 5 mM Bes or Pipes buffer, and 1 mM EGTA adjusted to pH 7.0 with TMAOH. Solubilized amphotericin B (500 µg/ml; ~45% purity, Sigma) was added to the pipette solution, after first dipping the tip into amphotericin-free solution. To investigate proton channels "enhanced gating mode" 60 nM PMA was used to stimulate the cells. The protein kinase C (PKC) inhibitor GF109203X (GFX; 3 µM) was used to revert the "enhanced gating mode." Holding potential for current families measurements was −60 mV. The holding potential for test pulses applied during application of either PMA or GFX was −30 mV.

Statistical Analysis.

Natural log transformations were performed for clinical measures of sperm production and fertility (e.g., total number of motile spermatozoa, days of abstinence) and superoxide production prior to analysis. Sperm progression and pH were recoded into three-level categorical variables≤2, 3, >3 and <8, 8-8.5, >8.5 respectively. The Kruskal-Wallis test was used to evaluate the relationship between pH (<8, 8-8.5, >8.5) and continuous measures of sperm characteristics including superoxide production, whereas Fisher's exact tests were used when the comparison was made with categorical measures of sperm characteristics. Correlations between continuous sperm characteristics and superoxide production were assessed using Spearman rank order correlations. Regression analyses were performed with sperm characteristics as the response variable and each of the ROS measures as explanatory variables. The regression models were run controlling for pH and log abstinence. All statistical tests were two-sided with a significance level of 5%. SAS software version 9.2 (SAS Institute, Cary, N.C.) was used throughout.

Dunnett's multiple comparison test was used for many of the in vitro experiments to adjust for multiple testing when comparing several means against the mean for a common control sample. A two-sided value of P<0.05 was accepted as significant.

The invention claimed is:

1. A method of assessing and treating male infertility comprising extracting proteins from a sperm or semen sample obtained from a subject and measuring the level of NOX5 protein in the sperm or semen sample, and contacting sperm or semen from which the sample was taken with NOX inhibitor 2-(2-chlorophenyl)-4-methyl-5-(pyridine-2-ylmethyl)1H-pyrazolo[4,3-c]pyridine-3,6(2H,5H)-dione (GKT136901) when NOX5 protein level is at least 10 fold higher than the NOX5 levels in a sperm or semen sample from a fertile donor.

2. The method of claim 1, further comprising measuring protein levels for cAb1 and HV1 proteins, wherein a decrease in protein levels is indicative of infertility.

3. The method of claim 1, wherein the level of NOX5 protein is at least 100 fold higher than the NOX5 levels in a sperm or semen sample from a fertile donor.

* * * * *